United States Patent [19]

Cassani et al.

[11] Patent Number: 4,956,180

[45] Date of Patent: Sep. 11, 1990

[54] AB-006 ANTIBIOTICS AND PROCESS FOR THEIR PRODUCTION

[75] Inventors: Giorgio Cassani, Arluno; Girgio Borgonovi, Milan; Dante Cidaria, Novara; Daniela Tolentino, Milan; Luigi Abis, Novara; Gianfranco Guglielmetti, Bogogno; Carlo Garavaglia, Cuggiono; Giovanni Confalonieri, Monza; Giorgio Pirali, Saronno, all of Italy

[73] Assignee: Presidenza Del Consiglio Dei Ministri, Rome, Italy

[21] Appl. No.: 418,928

[22] Filed: Oct. 6, 1989

Related U.S. Application Data

[63] Continuation of Ser. No. 213,768, Jun. 30, 1988, abandoned.

[30] Foreign Application Priority Data

Jul. 8, 1987 [IT] Italy .................. 21217 A/87

[51] Int. Cl.$^5$ .................. A61K 35/74; C12P 1/06
[52] U.S. Cl. .................. 424/118; 424/115; 435/169
[58] Field of Search .................. 424/115, 118; 435/169

*Primary Examiner*—Jerome D. Goldberg
*Attorney, Agent, or Firm*—Stevens, Davis, Miller & Mosher

[57] ABSTRACT

AB-006 Antibiotics and their AB-006 and AB-006b Antibiotic components, obtained by controlled aerobic culture of Streptomyces s.p. NCIB 12425, in an aqueous nutrient culture is disclosed. The AB-006 Antibiotics show biological activity, and in particular fungicidal and insecticidal activity.

12 Claims, 11 Drawing Sheets

AB-006 ANTIBIOTICS AND PROCESS FOR THEIR PRODUCTION

This application is a continuation of application Ser. No. 213,768, filed June 30, 1988, now abandoned.

DESCRIPTION OF THE INVENTION

The present invention relates to antibiotic substances, called arbitrarily AB-006 Antibiotics and to their components: AB-006a Antibiotic and AB-006b Antibiotic.

It also relates to the process for their preparation by fermentation of Streptomyces s.p. NCIB 12425, and to the use of said antibiotic substances in the treatment of contagious diseases caused by micro-organisms susceptible to said antibiotics.

The AB-006 Antibiotics are different from other known antibiotics.

By the term "AB-006 Antibiotics", used in the present invention, is meant a mixture comprising all the components having biological activity, for instance of the fungicidal and insecticidal type, produced by fermentation of Streptomyces s.p. NCIB 12425 under the conditions which are specified in detail hereinafter. Said active components comprise, but are not limited to, those indicated as AB-006a and AB-006b Antibiotics, which have been isolated from the mixture in accordance with the present invention.

As every person skilled in the art of fermentation will appreciate, the number and ratio of the components forming the AB-006 Antibiotics may vary, according to the fermentation conditions and the strain used.

Moreover, the present invention is not limited to the use of Streptomyces s.p. NCIB 12425, but it also comprises the use of natural or artificial mutants and variants of the aforesaid micro-organism, provided that they produce the AB-006 Antibiotics.

Therefore, the AB-006 Antibiotics form the principal object of the present invention, which antibiotics may be obtained by controlled aerobic culture of Streptomyces s.p. NCIB 12425 or by an equivalent mutant thereof, in an aqueous nutrient culture medium containing sources of carbon, nitrogen and inorganic salts, with subsequent separation of said antibiotics and of their AB-006a and AB-006b Antibiotic components.

PHYSICAL-CHEMICAL CHARACTERISTICS OF AB-006 ANTIBIOTICS.

Figure 1:
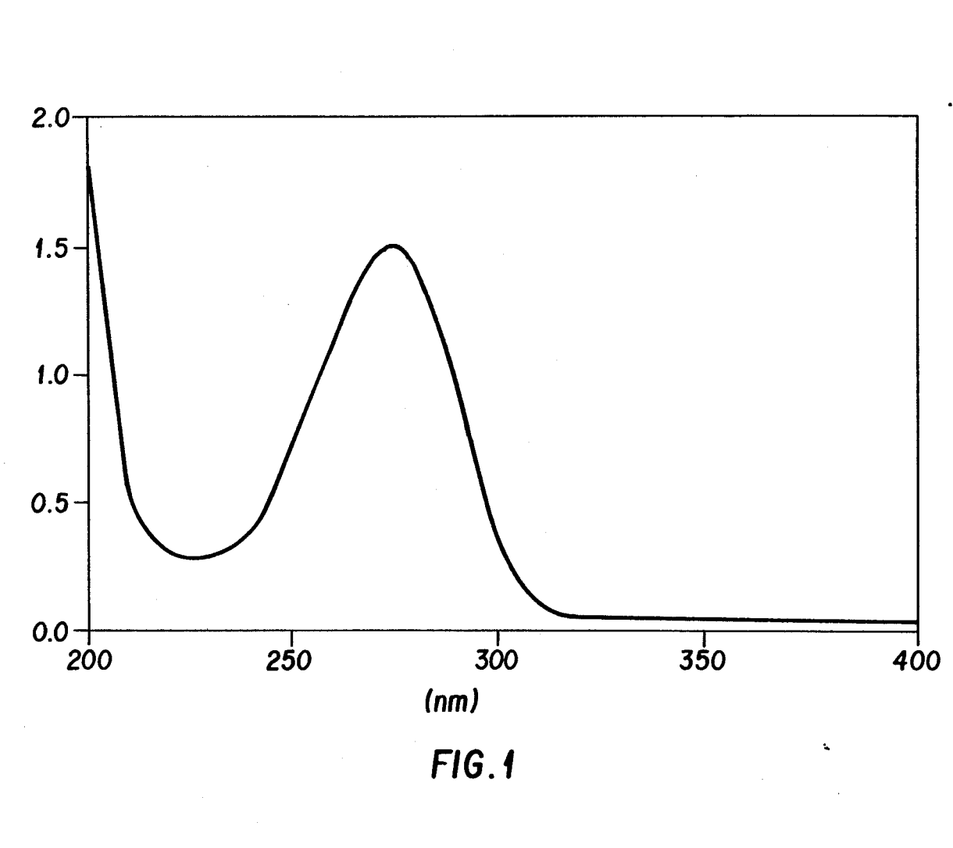

(a) The ultraviolet (U.V.) absorption spectrum is shown in FIG. 1 of the drawings. It presents an absorbance of 1.50 at 272 nm at a concentration of 0.1 mg/ml in water, and which remain invariant both in 0.1 N HCl and in 0.1 NaOH.

Figure 2:
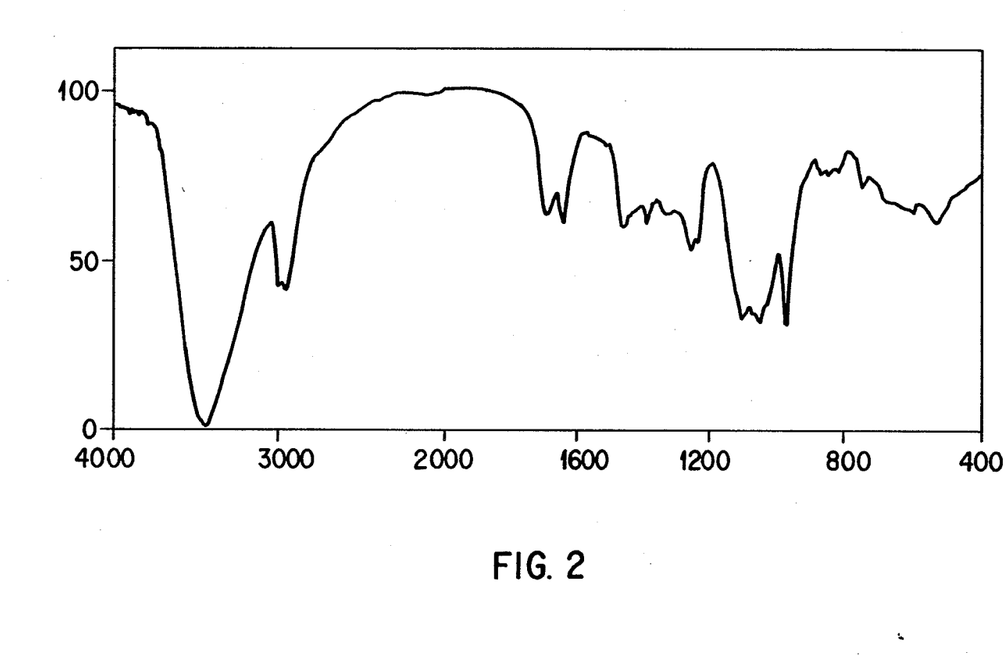

(b The infrared (I.R.) absorption spectrum in KBr tablet is shown in FIG. 2 of the drawings, and presents absorption maxima equal to those of the AB-006a and AB-006b Antibiotics, which will be described hereinafter.

PHYSICAL-CHEMICAL CHARACTERISTICS OF AB-006a ANTIBIOTIC.

Figure 3:
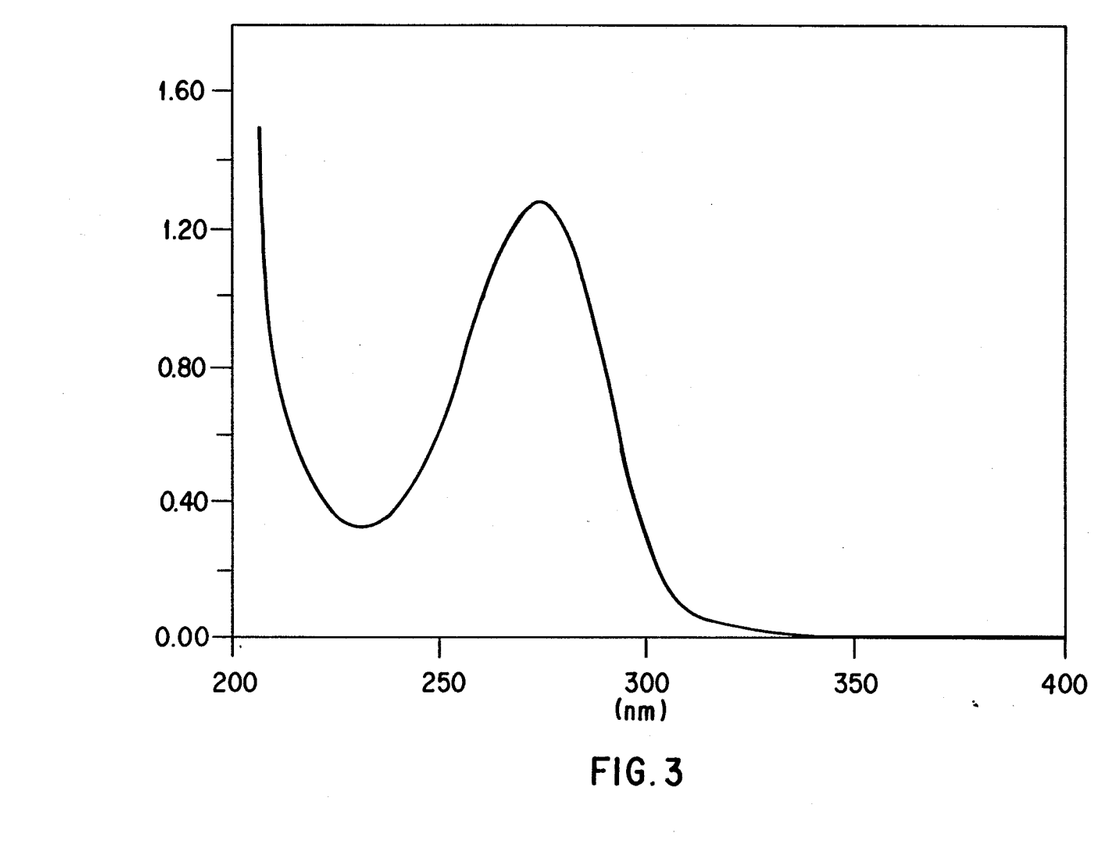
Figure 4:
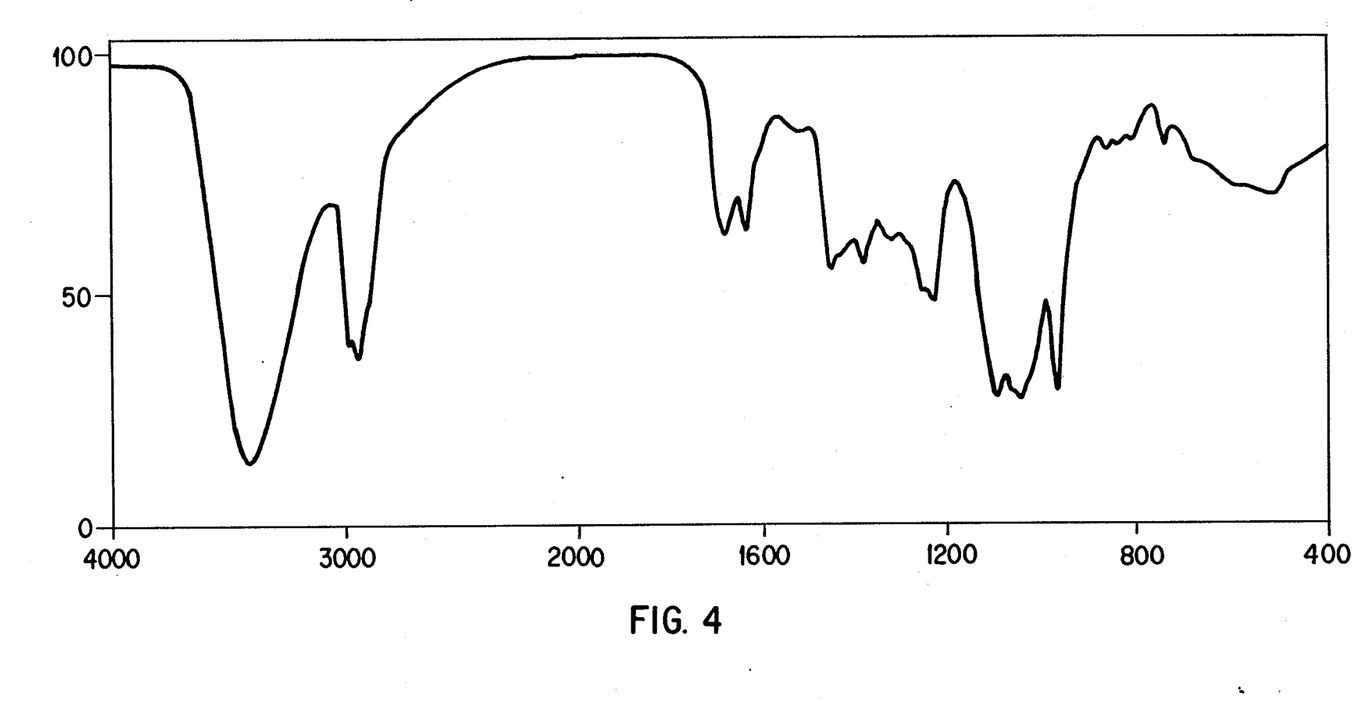
Figure 5:
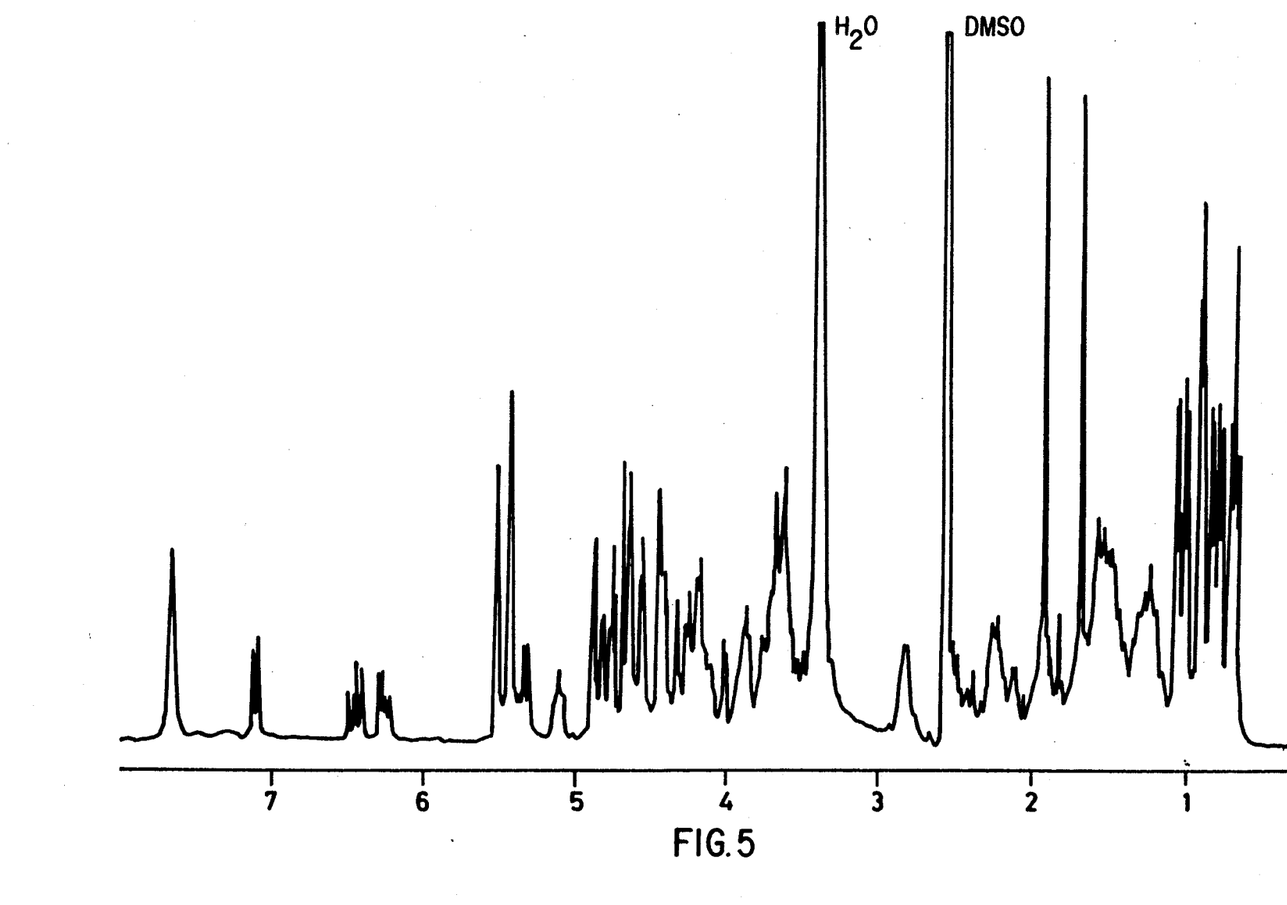
Figure 6:
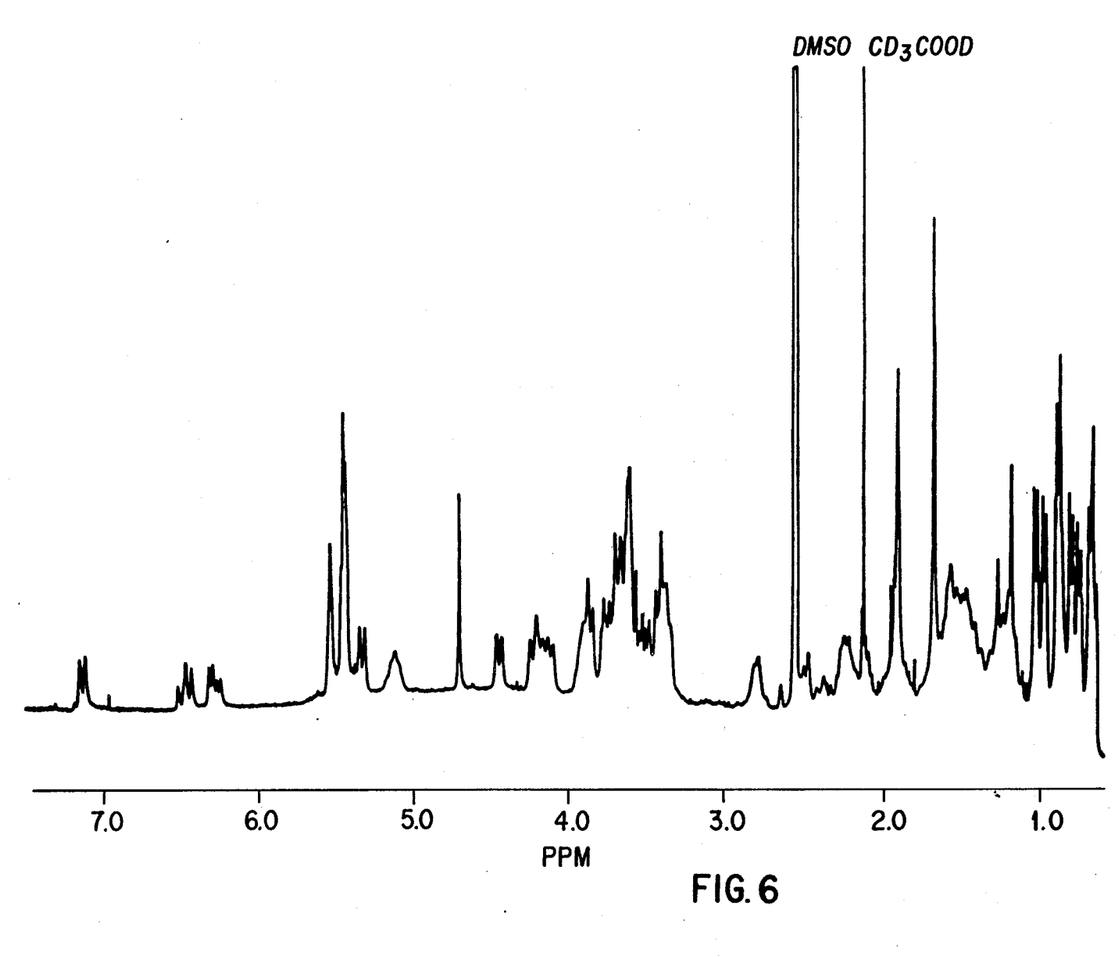

The AB-006a Antibiotic, a component of the ASB-006 antibiotics, appears as a white-hazel powder characterized by:

(a) good solubility in dimethyl sulfoxide and in mixtures ethanol/water (1:1, V/V) or methanol/water (1:1, V/V), and poor solubility in water, ethanol or methanol;

(b) approximate elemental analysis, determined on a sample kept under vacuum at 40° C. for 2 hours, in percentage: carbon 54.94, hydrogen 8.64, nitrogen 1.08;

(c) molecular weight of about 1203, as deduced from FASB-MS spectrum showing an $(M+H)^+$ peak 1204, under the following operating conditions:
Positive ions FAB, Xe
Acceleration voltage, 9.5 KV
Glycerol matrix
Finningan Mat 8424;

(d) the ultraviolet (UV) absorption spectrum is shown in FIG. 3 of the drawings. It presents a maximum absorbance of 1.27 at 272 nm at a concentration of 0.1 mg/ml in water, which remains invariant both in 0.1N HCl and in 0.1N NaOH;

(e) the infrared (IR) absorption spectrum in KBr tablet is shown in FIG. 4 of the drawings and presents the following absorption maxima ($cm^{-1}$):
3700–3060, 2970, 2930, 2980 (shoulder), 1685, 1635, 1570–1505, 1455, 1435 (shoulder), 1385, 1355–1310, 1255 (shoulder), 1235, 1100, 1085–1000, 975, 875, 850, 820, 750;

(f) the $1_H$ NMR spectrum is shown in FIG. 5 and presents signals recorded by means of a spectrometer BRUKER AM 300 NHz in hexadeutero dimethylsulfoxide (DMSOd6). The chemical shifts were referred indirectly to TMS=0.00 ppm($\delta$TMS) by using, as internal reference, the central peak of hexadeutero dimethylsulfoxide taken at $\delta$TMS=2.56 ppm:

TMS (ppm): 0.68 (d, 3H); 0.71 (d, 3H); 0.78 (d, 3H); 0.83 (d, 3H); 0.89 (d, 3H); 0.92 (d, 3H); 1.00 (d, 3H); 1.05 (d, 3H); 1.1–1.65 (~14H); 1.69 (s, 3H); 1.93 (s, 3H); 2.00–2.55 (~6H); 2.81 (m, 2H); 3.25–3.54* (~5H); 3.55–4.00 (~11H); 4.02–4.89 (22H among which 17H are mobile); 4.19* (m, 3H); 4.42* (d, 1H); 4.69* (s, 1H); 5.11 (t, 1H); 5.32 (d, 1H); 5.44 (m, 4H); 5.53 (s, 2H); 6.26 (dd, 1H); 6.46 (dd, 1H); 7.11 (d, 1H); 7.67 (s, 2 mobile H). The signals with asterisk at ppm 3.25–3.54, 4.19, 4.42 and 4.69, which cannot be integrated with this spectrum, as they are masked by other mobile hydrogen ions, were individualized by addition of deutero acetic acid ($CD_3COOD$) as shown by the spectrum of FIG. 6. For the H number assigned to the signal groups, an error not lower than 5–10% is valued, owing to the difficulty in setting correctly the spectrum.

Figure 7:
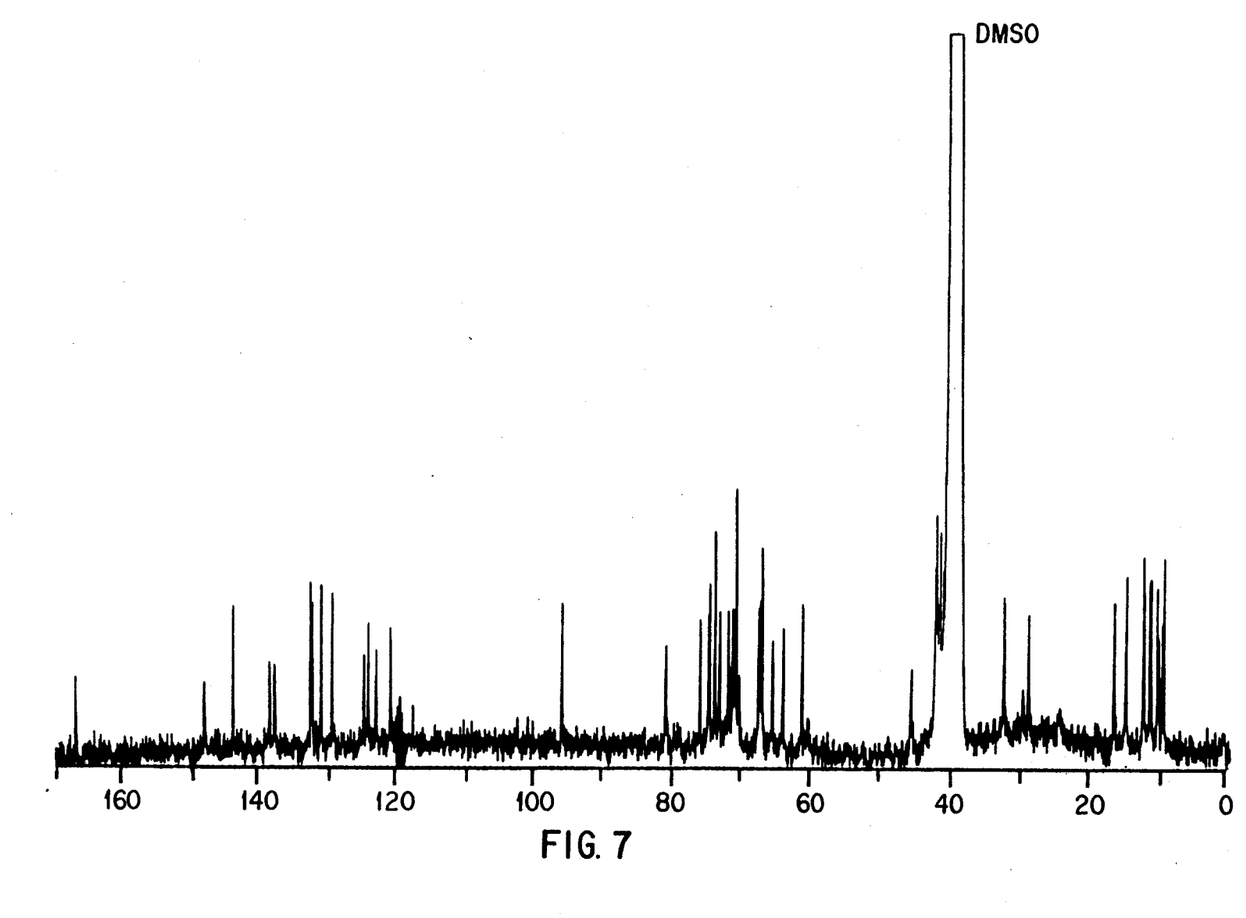

(g) The NMR spectrum of $^{13}C$ is shown in FIG. 7 and presents signals recorded by means of a spectrometer BRUKER AM 300 MHz in hexadeutero-dimethylsulfoxide (DMSOd6). The chemical shifts were referred indirectly to TMS=0.00 ppm($\delta$TMS), by using as internal reference the central peak of deuterodimethylsulfoxide taken at $\delta$TMS=39.85 ppm.

$\delta$TMS (ppm): 9.66; 9.77; 10.30; 10.55; 11.37; 11.61; 12.53 15.00; 16.81; 29.03; 29.16; 29.58; 32.28; 32.50; 39.20*; 39.38*; 39.68*; 41.74*; 42.0–1*; 42.46*; 42.46*; 42.63;*; 45.95; 61.30; 63.84; 65.19; 66.69; 66.81; 67.11; 67.36; 70.14; 70.38; 70.58; 71.10; 71.59; 72.89; 73.63; 73.77; 74.54; 75.80; 81.02; 95.82; 120.90; 122.86; 124.23; 125.05; 129.56; 131.19; 132.43; 132.78; 138.00; 138.65; 144.02; 148.17; 167.22.

The asterisk (*) indicates the peaks covered with DMSO, individualized by means of the DEPT technique at 45°.

(h) The retention coefficients in thin layer chromatography with an eluent run of 15 cm on silica Kieselgel 60 F 254 (Merk-Schuchardt) plates and on silica in reversed phase RP-18 F 254 (Merk-Schuchardt) plates in the following eluent systems and compared with the AB-006b Antibiotic:

eluent A=n-butanol: acetic acid: water 3:1:1)

eluent B=n-butanol: acetic acid: water: ethanol (38:10: 50:2)

eluent C=1% (w/v) ammonium carbonate in water: tetrahydrofuran (1:2)

eluent D=tetrahydrofuran: trifluoroacetic acid 0.14 mM in water: methanol (3:6:1)

eluent E=monobasic potassium phosphate 33mM+tetramethyl ammonium chloride 10 mM in water: methanol (1:4);

| Plate  | Eluent | (Rf) AB-006a | (Rf) AB-006b |
|--------|--------|--------------|--------------|
| silica | A      | 0.34         | 0.39         |
| silica | B      | 0.20         | 0.16         |
| RP-18  | C      | 0.20         | 0.43         |
| RP-18  | D      | 0.09         | 0.13         |
| RP-18  | E      | 0.58         | 0.67         |

Visualization:
A. UV light fluorescence
B. Ninhydrin
C. Reagent of Dragendorff (modified by Munier and Macheboeuf)

Thin Layer Chromatography - Page 873 - Author: Egon Stahl

Second Edition - Publisher: Springer-Verlag Berlin. Heildelberg, New York 1969.

(1) Retention time (Rt) of 10.75 minutes if analyzed on an HPLC column in reversed phase under the following conditions:

Column=cartridge ROSIL C 18 (5 microns) 150 ×4.6 mm ALLTECH ITALY - 20139 Milan - Italy Precolumn=Guard Pak RCSS C 18 Millipore S.p.A. - 20090 Segrate (Milan) - I Eluent A=Monobasic potassium phosphate 7 mM+tetramethyl ammonium chloride 7 mM : methanol (1:1)

Eluent B=methanol

Elution=linear gradient from 40% to 70% of eluent B in eluent A in 14 minutes

Flow=1.2 ml/min

UV detector 270 nm

Temperature=30° C.

Under the same conditions the retention time of the AB-006b Antibiotic is 8.25 minutes.

Or retention time (Rt) of 7.1 minutes, if analyzed on a HPLC column in reversed phase under the following conditions:

Column=Cartridge Hibar LiChroCART LiChrosorb RP-18 250×4 mm (E. Merck, Darmstadt, F.R. Germany)

Precolumn=Guard Pack RCSS C 18 (Millipore Waters)

Eluent=0.1% ammonium carbonate in water:tetrahydrofuran (65:35)

Flow=1 ml/min

UV detector 270 nm

Temperature=30° C.

Under the same conditions the AB-006b Antibiotic is eluted after 6.0 minutes.

Figure 8:
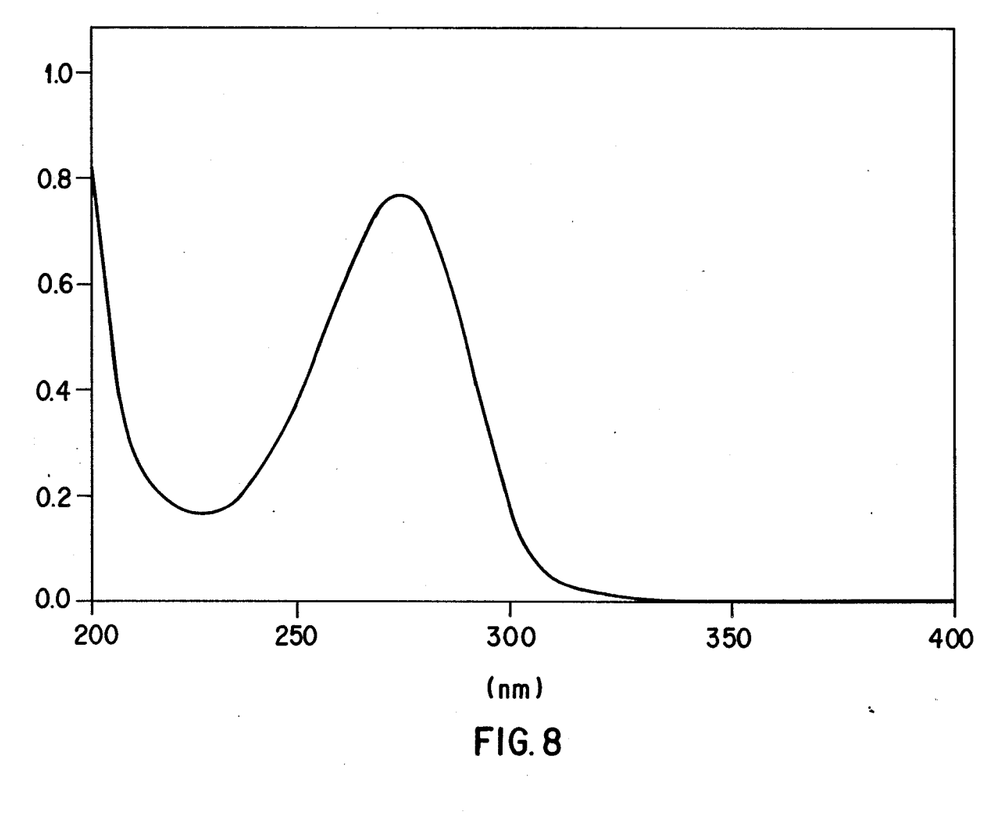

PHYSICAL-CHEMICAL CHARACTERISTICS OF THE AB-006b ANTIBIOTIC (a) The ultraviolet (UV) absorption spectrum is shown in FIG. 8 of the drawings. It presents a maximum absorbance of 0.77 at 272 nm at a concentration of 0.02 mg/ml in water, which remains unvaried both in 0.1N HCl and in 0.1N NaOH.

Figure 9:
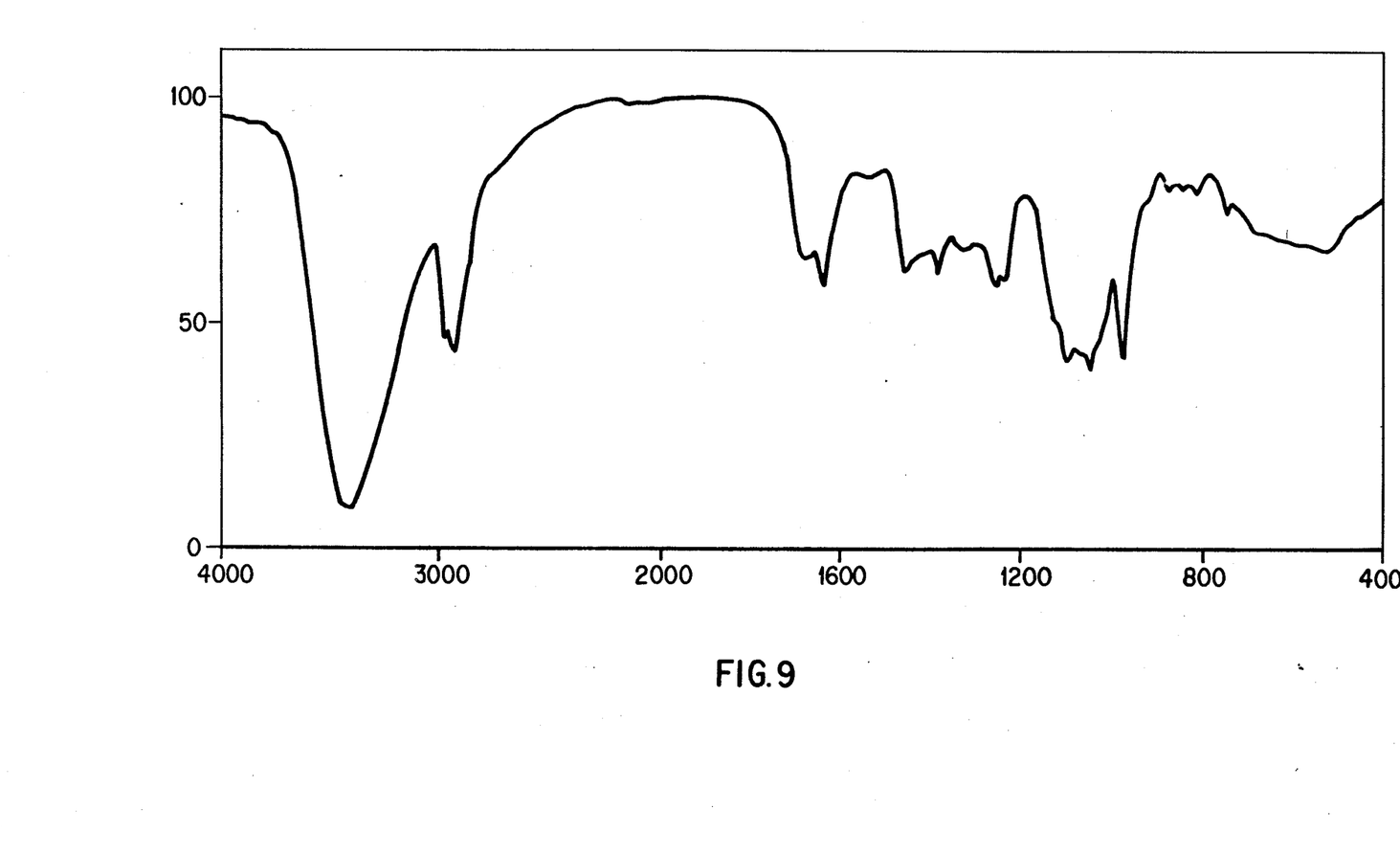

(b) The infrared (IR) absorption spectrum in KBr tablet is shown in FIG. 9 of the drawings and presents absorption maxima (cm$^{-1}$) equal to those of the AB-006a Antibiotic.

Figure 10:
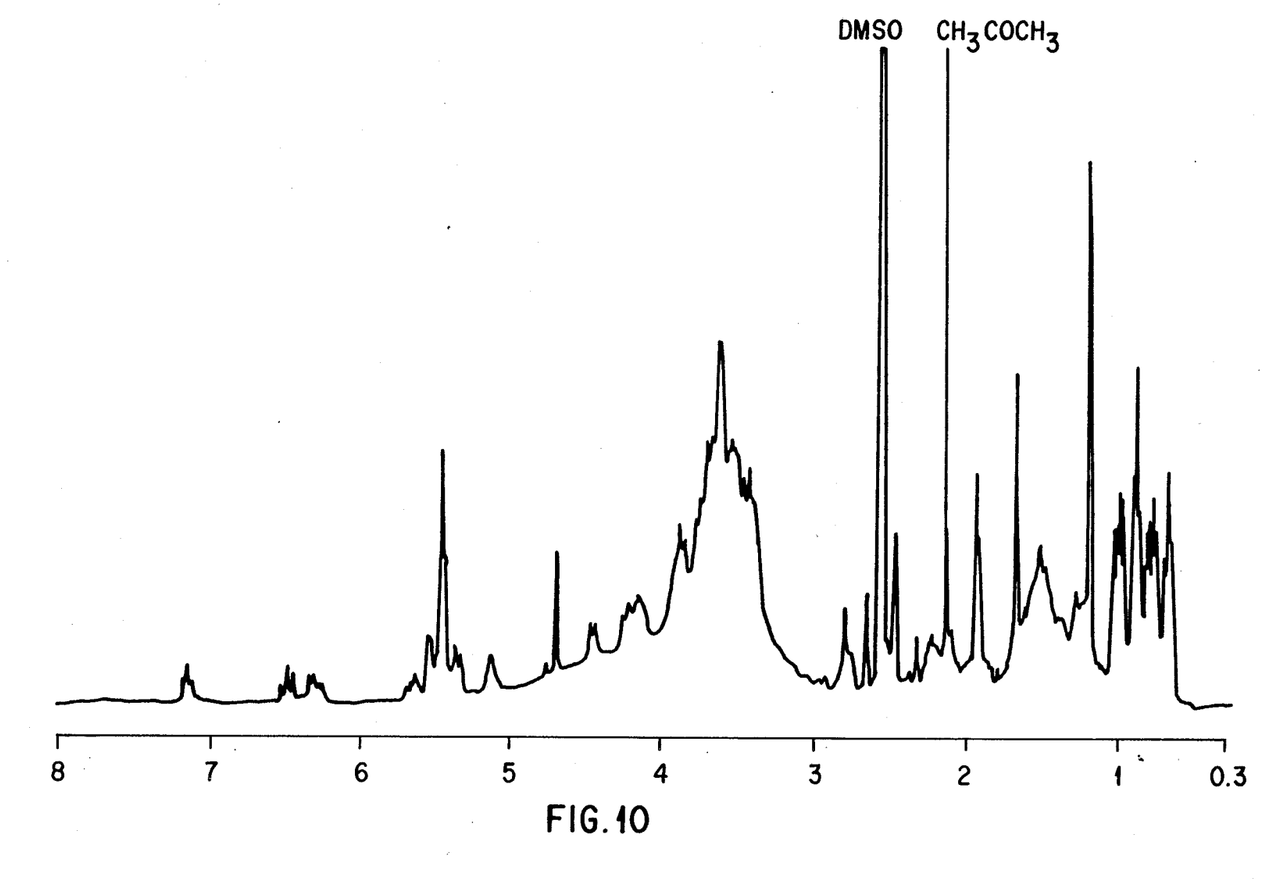

(c) The NMR spectrum of $^1$H is shown in FIG. 10 and presents signals recorded by means of a BRUKER AM 300 MHz spectrometer in hexadeutero-dimethylsulfoxide (DMSOd6). The chemical shifts were referred indirectly to TMS=0.00 ppm ($\delta$TMS) by using, as internal reference, the central peak of dimethylsulfoxide taken at $\delta$TMS=2.56.

Figure 11:
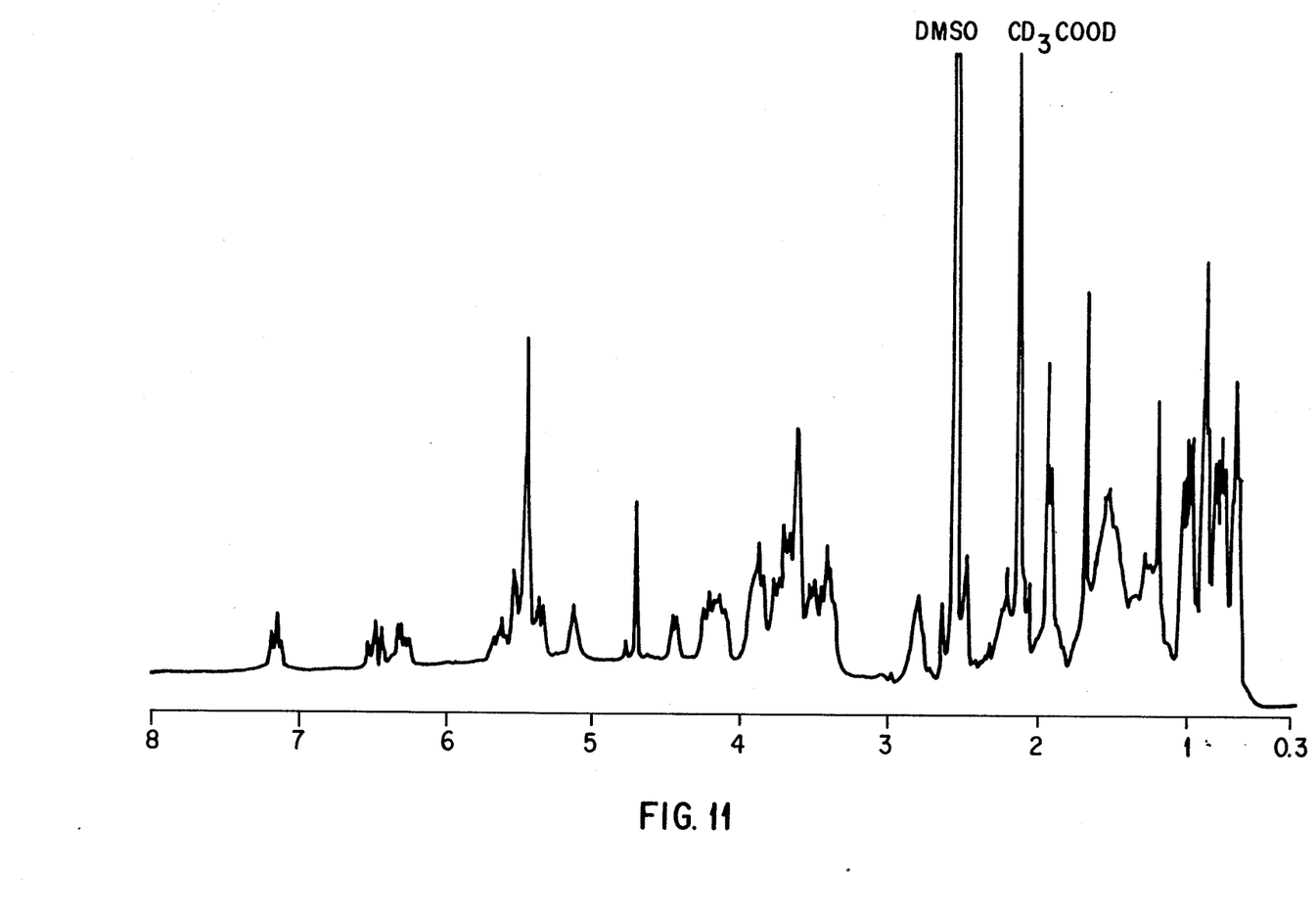

$\delta$TMS (ppm): 0.69 (d, 3H); 0.71 (d, 3H); 0.78 (d, 3H); 0.83 (d, 3H); 0.89 (d, 3H); 0.92 (d, 3H); 1.00 (d, 3H); 1.04 (d, 3H); 1.21 (s); 1.69 (s, 3H); 1.96 (s, 3H); 1.1–2.4 ($\sim$35H); the signals at ppm: 1.21, 1.69, 1.93; 2.8 (m, 2H) included; 2.9–5.0 group of signals overlapped upon mobile H ions; 3.3–4.0* (20H); 4.16* (m, 3H); 4.43* (d, 1H); 4.69* (s, 1H); 5.11 (t broad, 1H); 5.2-5.8 ($\sim$10H) 6.26 (dd, 1H); 6.43 (dd, 1H); 7.12 (t, 1H);

The signals with asterisk at ppm 3.3–4; 4.16; 4.43 and 4.69, which cannot be integrated with this spectrum, as they are masked by other mobile hydrogen ions, were shown by addition of deuteroacetic acid (CD$_3$COOD) as proved by NMR spectrum of 1H of FIG. 11.

For the H number assigned to the signal groups, an error not lower than 5–10% is valued, owing to the difficulty in setting correctly the spectrum.

(d) The retention coefficients (Rf) in thin layer chromatography and the retention times on HPLC in reversed phase, are reported respectively in paragraphs h and i of the description of the characteristics of AB-006a Antibiotic.

MORPHOLOGY AND CULTURE CHARACTERISTICS OF THE MICRO-ORGANISM STREPTOMYCES S.P. NCIB 12425

The micro-organism was isolated from a sample of soil picked up at Cassano d'Adda (Milan), cataloged with the conventional name SD35.

A culture of this microorganism was filed on the 1st of April 1987, according to the Budapest treaty, by the National Collection of Industrial Bacteria (c/o The National Collection of Industrial and Marine Bacteria Ltd., Torry Research Station, P.O. Box 31, 135 Abbey Road, Aberdeen AB 98 DG, Scotland - U.K.), where admission number NCIB 12425 was granted to it.

The morphological characteristics of the strain are set forth in Table A (the names of the media are those set forth by the International Streptomyces Program).

| Abbreviation ISP | Culture Medium | Description |
|------------------|----------------|-------------|
| M1 | Tryptone-yeast extract broth | Plentiful growth, lack of soluble pigment. |
| M2 | Malt extract agar | Plentiful growth, basal mycelium without any characteristic coloring; plentiful aerial mycelium; grey-colored spores; it does not form any soluble pigment. |
| M3 | Oat-meal agar | Plentiful growth, basal mycelium without any characteristic coloring; plentiful aerial mycelium, white colored |

| Abbreviation ISP | Culture Medium | Description |
|---|---|---|
| | | spores; it does not form any soluble pigment. |
| M4 | Starch agar | Plentiful growth, basal mycelium without any characteristic coloring; plentiful aerial mycelium, grey-colored spores; it does not form any soluble pigment. |
| M5 | Glycerol-asparagine agar | Plentiful growth, basal mycelium without any characteristic coloring; plentiful aerial mycelium, grey-colored spores; it does not form any soluble pigment. |
| M6 | Peptone-iron agar | Poor growth, basal mycelium without any characteristic coloring; poor aerial mycelium, grey-colored spores; it does not form any soluble pigment. |
| M7 | Tyrosine agar | Poor growth, basal mycelium without any characteristic coloring; poor aerial mycelium, grey-colored spores; it does not form any soluble pigment. |
| — | Nutrient agar | Poor growth, basal mycelium without any characteristic coloring; white-colored spores; it does not form any soluble pigment. |
| — | Potato dextrose agar | Plentiful growth, basal mycelium without any characteristic coloring; poor aerial mycelium, white-colored spores; it does not form any soluble pigment. |
| — | Nutrient gelatin | Poor growth, no hydrolysis reaction of gelatin is observed. |
| — | Litmus milk | Poor growth, no characteristic reaction is observed. |

In Table B the growth is set forth of strain SD35 on a few organic compounds, as the only source of carbon.

TABLE B

| Compound | Growth |
|---|---|
| 2-keto-gluconate | − |
| adonitol | − |
| arabinose | + |
| cellobiose | + |
| fructose | + |
| galactose | + |
| glycerol | + |
| glucose | + |
| inositol | + |
| lactose | + |
| maltose | + |
| mannitol | + |
| melzitose | − |
| methyl-D-glucoside | − |
| N-acetyl-D-glucosamine | + |
| raffinose | − |
| ramnose | + |
| saccharose | − |
| sorbitol | − |
| trehalose | + |
| xylitol | − |
| xylose | + |

+ shows a positive growth.
− shows lack of growth.

The analysis of the cellular wall of strain SD35 carried out by the method described by M. P. Starr, H. Stolp, H. G. Truper, A. Ballows, H. G. Shegel (the Prokaryotes - Vol. II Streptomycetacee - Springer Verlag Ed. 1981) shows lack of characteristic sugars, and therefore strain SD35 is confirmed to belong to Streptomyces genus.

As with other micro-organisms, Streptomyces s.p. NCIB 12425 may undergo changes. For instance, artificial variants of mutants may be obtained by treatment with different known mutagens, such as X- or ultraviolet (U.V.) rays, high frequency waves and chemical substances such as nitrous acid, halogenated alkyl amines, nitrosoguanidine, camphor, and the like.

All the natural and artificial variants and mutants belonging to the Streptomyces species and producing the AB-006 Antibiotics are considered as equivalent to the strain—Streptomyces s.p. NCIB 12425 and are included within the scope of the present invention.

PROCESS FOR PREPARING THE AB-006 ANTIBIOTICS

The process for preparing the AB--006 Antibiotics consists in growing Streptomyces s.p. NCIB 12425, or an equivalent mutant thereof, under conditions of controlled aerobic fermentation, in an aqueous nutrient medium and, in separating said antibiotics by per se known methods.

Although use may be made of any culture nutrient media or fermentation broths usually employed for producing antibiotics, certain culture media are, however preferred. Said culture media must contain carbon and nitrogen sources assimilable by microorganisms of the Streptomyces genus and, furthermore, low contents of inorganic salts. Moreover, they must contain traces of those metals which are necessary for the growth and development of the microorganisms. Said trace metals may already be present as impurities in the sources of carbon or proteinic nitrogen supplied for the bacterial growth or if necessary they may be added to the culture medium.

In general, as carbon source use may be made of carbohydrates, and in particular saccharides such as, for instance, dextrose, maltose, lactose or, alternatively or supplementary, the amides and industrial products that may be compared chemically to the amides such as, for instance, dextrin, soluble starch, or polyalcohols such as glycerol as well. Such compounds can be used singly or in combination.

The concentration of the carbon source in the culture medium generally depends on the kind and amount of the other ingredients of the medium; however, concentrations ranging from 0.5 to 5% by weight are generally satisfactory.

As nitrogen source use may be made of proteinic extracts such as, for instance, yeast extract, hydrolyzed casein, or meals such as, for instance, soya meal, or industrial products which are on sale for this purpose such as, for instance, Proflo, corn steep liquor, distillers solubles, etc.

These compounds can be used singly or in combination, in concentrations, in the culture medium, ranging from 0.2 to 6% by weight.

As inorganic salts, use may be made of for instance sodium, potassuium, magnesium, ammonium, and calcium salts such as of phosphates, sulfates, chlorides, carbonates, and nitrates.

The metals present in trace amounts may be, for instance, cobalt, manganese, iron, and the like.

A few culture media show a particular capability for stimulating the production of the AB-006 Antibiotics from Streptomyces s.p. NCIB 12425 such as, for instance, the following aqueous formulations, which are used in the subsequent preparation examples:

|  | (concentration g/l) |
| --- | --- |
| CULTURE MEDIUM A (ingredients) | |
| starch | 20 |
| glucose | 10 |
| calcium carbonate | 3 |
| hydrolyzed casein | 2 |
| Proflo | 2 |
| yeast extract | 2 |
| meat extract | 2 |
| CULTURE MEDIUM B (ingredients) | |
| glycerol | 30 |
| Proflo | 20 |
| calcium carbonate | 3 |
| CULTURE MEDIUM C (ingredients) | |
| tryptone | 10 |
| meat and liver peptone | 10 |
| glucose | 5 |
| yeast extract | 5 |
| $K_2HPO_4$ | 1 |

The strain of Streptomyces s.p. NCIB 12425 may be grown at temperatures ranging from 20° to 35° C., and preferably from 25° to 30° C.

The pH conditions may generally range from about 5 to 9.

The sterile air, which is insufflated into the culture medium, is generally used in such amounts as to maintain in the medium an oxygen concentration higher than 20%.

The production of antibiotics during the fermentation can be monitored by means of tests for antibiotic activity on samples of the broth.

The fermentation is carried out for a period of time such as to obtain a substantial antibiotic activity. Periods of time of 48-92 hours are generally sufficient.

SEPARATION AND PURIFICATION OF THE ANTIBIOTICS.

After the culture under the fermentation conditions described hereinbefore, the AB-006 Antibiotics and the AB-006a and AB-006b Antibiotic components may be separated from the culture broth and subsequently purified by methods which are customary and per se well known in the fermentation art.

Such methods include, for instance, extraction by means of solvents, precipitation by means of non-solvents, ultrafiltration, column chromatography, silica gel chromatography, cellulose chromatography, reversed phase chromatography on macroporous non-ionic resins, and the like.

The antibiotics produced during the fermentation are in the culture broth and/or in the mycelium mass.

A preferred method for recovering the AB-006 Antibiotics consists in separating by filtration the mycelium mass from the culture broth, in extracting the mycelium thus separated by means of acetone or methanol, in concentrating the extract under vacuum till the solvent is completely removed, thereby obtaining an aqueous suspension from which, by addition of acetonitrile, the AB-006 Antibiotics are partly precipitated and then separated as raw product A.

The clarified filtrate obtained from the mycelium separation is ultrafiltered on a DIAFLO YM5 (Amicon Co.) membrane till the retentate reaches 1/10 of its starting volume; the retentate is then diluted 3 times with water and ultrafiltered again up to ⅓ of its volume, and afterwards this last retentate is discarded.

The two permeates or ultrafiltrates, as obtained previously, are collected and passed through a column made of a non-ionic polystyrene resin, for instance, of type XAD-4 (Rohm & Haas Co.), which absorbs the AB-006 Antibiotics.

Then the resin is rinsed with two volumes, referred to its bed, of water, afterwards it is eluted with three volumes, referred to its bed, of a mixture containing 50% (v/v) of acetonitrile in water.

The fractions containing the AB-006 Antibiotics, individualized by means of biological tests of activity on Pythium, are again collected and concentrated to dryness to yield a raw product B containing the AB-006 Antibiotics.

Then the pure AB-006a and the pure AB-006b Antibiotics are isolated from A and B raw products by reversed phase chromatography by using a column filled with silica type MATREX Silica C18 (Amicon Europe, Lausanne, CH), with an eluent system consisting of eluent A consisting of water containing 33 millimoles/1 of $KH_2PO_4$ and 10 millimoles/1 of tetramethylammonium chloride and of eluent B consisting of methanol, by using a linear gradient from 50 to 70% of eluent B in eluent A.

The fractions containing the pure AB-006a and pure AB-006b Antibiotics, are then purified from the salts by passing said fractions separately through a resin type XAD-4. These fractions are then rinsed with water till disappearance of phosphate and chloride ions, and afterwards they are eluted with a mixture containing 50% (v/v) of acetonitrile in water and finally concentrated to dryness.

Optionally resin XAD-4 may be replaced by other polystyrene resins, cross-linked with divinylbenzene.

Other materials such as, for instance, activated carbon may be used to adsorb the AB-006 Antibiotics.

Moreover one may extract the antibiotics by using highly polar solvents such as, for instance, 1-butanol.

The plane membranes for ultrafiltration may be replaced, optionally, by hollow fibers or by spiral membrane systems.

Furthermore, to elute the AB-006 Antibiotics from different adsorbents, use may be made of mixtures of solvents mixible with water such as, for instance: methanol, acetonitrile, tetrahydrofuran, ethanol, dimethylformamide, and dimethylsulfoxide.

BIOLOGICAL ACTIVITY

The AB-006 Antibiotics and their AB-006a and AB-006b components are endowed with fungicidal and insecticidal activity.

Their fungicidal activity turns out to be particularly high towards phytopathogenous fungi infesting cereal cultivation, fruit-growing, as well as industrial and horticultural cultivations.

The fungicidal activity of the AB-006 Antibiotics, both "in vitro" and "in vivo", was determined by methods described below.

FUNGICIDAL ACTIVITY "IN VITRO"

This test was carried out by incorporating a part of a suitable solution of the AB-006 Antibiotics into nutrient agar, fit for the growth of phytopathogenous fungi (for instance: potato dextrose agar), hot dissolved and cooled to 45° C.; after incorporation the agar was permitted to gel at room temperature. Then the Petri plates containing the agar were inoculated by placing, at the edge of the plate, a fragment of the fungus colony and incubating at 20° C. for about a week.

When the incubation period was over, the growth radii of the fungus colonies were measured. These radii were related to the growth in control tests (inoculated plates containing only the nutrient medium to which no AB-006 Antibiotic had been added) and the results were expressed as inhibition percentage.

FUNGICIDAL ACTIVITY "IN VIVO"

Here the activity was measured by using the following method: Plants, grown in pots in a conditioned environment, were sprayed on their lower leaf face with AB-006 Antibiotics in a water-acetone solution containing 20% of acetone (v/v).

Then the plants were kept in a conditioned environment for one day, and afterwards they were sprayed on their upper leaf face by inoculating the fungus being tested. Then the plants were carried back into a conditioned environment.

At the end of the incubation period of the fungus (eight days), the degree of infection was evaluated by means of indices on an evaluation scale ranging from 100 (=sound plant) to 0 (=completely infected plant).

The data relating to the main activities "in vitro" are set forth in Table C, whereas the data relating to the preventive activities "in vivo" are set forth in Table D.

TABLE C

| Fungus | AB-006 ANTIBIOTICS DOSE (ppm) | % OF GROWTH INHIBITION |
|---|---|---|
| Cercospora | 20 | 100 |
| beticola | 30 | 100 |
|  | 40 | 100 |
| Cercosporella | 20 | 100 |
| herpetrichoides | 30 | 100 |
|  | 40 | 100 |
| Helminthosporium | 20 | 100 |
| gramineum | 30 | 100 |
|  | 40 | 100 |
| Helminthosporium | 20 | 100 |
| sativum | 30 | 100 |
|  | 40 | 100 |
| Sclerotium | 20 | 100 |
| cepivorum | 30 | 100 |
|  | 40 | 100 |
| Rhizoctonia | 20 | 100 |
| solani | 30 | 100 |
|  | 40 | 100 |
| Botrytis | 20 | 100 |
| cinerea | 30 | 100 |
|  | 40 | 100 |
| Colletotrichum | 20 | 100 |
| coffeanum | 30 | 100 |
|  | 40 | 100 |
| Pythium | 20 | 100 |
| irregulare | 30 | 100 |
|  | 40 | 100 |

TABLE D

| FUNGUS | AB-006 ANTIBIOTICS Concentration (g/l) | PREVENTIVE ACTIVITY |
|---|---|---|
| Plasmopara | 3 | 100 |
| viticola | 6 | 100 |
| Sphaeroteca | 3 | 100 |
| fuliginea | 6 | 100 |
| Botrytis | 3 | 100 |
| cinerea | 6 | 100 |

Strictly similar results of fungicidal activity were obtained by using the single Antibiotics: AB-006a and AB-006b.

For their practical uses, both in agriculture and in other fields, it is useful to use the antibiotics according to this invention in the form of suitable compositions.

These compositions contain, besides an antibiotic according to the invention as active principle, inert solid vehicles (for instance, kaolin, silica, talc, attapulgite, diatomaceous earth, and the like) or inert liquid vehicles (organic solvents, vegetable or mineral oils, water and mixtures thereof) and, optionally, other additives in customary use in the formulations field such as surfactants, suspending agents, dispersants, and wetting agents.

For particular application needs or in order to increase the application spectrum of the compositions, other active ingredients such as, for instance insecticides, herbicides, fungicides or fertilizers, may be added to the above-described compositions.

The application doses vary, depending on different factors, such as the kind of infestation and its degree, the kind of composition used, climatic and environmental factors, etc.

For practical use in agriculture, doses of antibiotics ranging from 10 to 500 g/ha give satisfactory results.

A few examples will follow, by way of illustration, but not by way of limitation, of the invention.

EXAMPLE 1

Fermentation of strain Streptomyces s.p. NCIB 12425

A 2000 ml flask, containing 500 ml of culture medium A, as described hereinbefore, was inoculated with a lyophilized phial of Streptomyces s.p. NCIB 12425 and set to incubate on a rotary shaker (100 rpm) at 28° C. over 72 hours.

The micro-organism culture thus obtained was utilized to inoculate a 10 l fermentation apparatus, containing 7 liters of culture medium B, as described above.

The fermentation bulk was incubated over 96 hours, keeping it at the temperature of 28° C., and by using an air flow of 60 l/h and a stirring rate of 300 rpm.

Then the fermentation broth was unloaded and sent to the subsequent operations of separation and purification.

Separation of the AB-006 Antibiotic

The 7 liters of fermentation broth, obtained in the preceding step, were filtered on paper and the separated mycelium was extracted with methanol.

The methanolic extract was concentrated under vacuum till disappearance of the solvent and, from the remaining aqueous suspension, the AB-006 Antibiotics were precipitated by addition of 4 volumes of acetonitrile. The thus-obtained precipitate was dissolved in methanol/water (1,1), then separated by filtration from the suspended impurities, after which it was concentrated to yield a raw product A containing the AB-006 Antibiotics coming from the mycelium.

The clarified broth, obtained from the filtration on paper of the mycelium, was ultrafiltered on membrane DIAFLO YM 5 (Amicon Co.) till the retained part reached a volume of 0.7 l.

The retenate (0.7 l) was diluted three times with water and ultrafiltered again till a further retentate of 0.7 l was obtained, which was eliminated.

The two ultrafiltrates or permeates, obtained from the two ultrafiltration described above, were collected and conveyed, with a flow of 0.9 l/h, into a column having an inner diameter of 8 cm filled with 0.7 kg of resin XAD-4.

The column was rinsed with 2 l of water and eluted with a 1:1 mixture of acetonitrile/water.

The fractions containing the AB-006 Antibiotics, individualized by high performance liquid chromatography (HPLC), were collected, then concentrated till removal of most of the acetonitrile, after which they were subjected to chromatography again on the same column of resin XAD-4, under the conditions described above. The collected fractions, containing the AB-006 Antibiotics, were concentrated to dryness to yield a raw product B containing the AB-006 Antibiotics coming from the fermentation broth after mycelium separation.

Separation and purification of the AB-006a Antibiotic and AB-006b Antibiotic, components of the mixture of AB-006 Antibiotics.

The two raw products A and B, coming from the preceding separation step and containing the AB-006 Antibiotics, were collected and subjected to reversed phase chromatography in a column, filled with silica gel type MATREX Silica C18, (Amicon Co.), having an inner diameter of 2.2 cm and 30 cm in length, with a flow of 1.7 ml/min. and by using successively the following volumes of an eluent system, each of them consisting of eluent A and eluent B in the proportions as indicated hereinafter:

| Eluent System ml | Ratio Eluent A/Eluent B v/v |
| --- | --- |
| 350 | 50/50 |
| 200 | 40/60 |
| 800 | 30/70 | wherein:

eluent A = an aqueous solution containing 33 mM of $KH_2PO_4$ and 10 mM of tetramethylammonium chloride; and eluent B = methanol.

The fraction of 120 ml was collected in the elution range from 550 to 670 ml, containing the AB-006b Antibiotic, and subsequently the fraction of 360 ml was collected in the elution range from 930 to 1290 ml, containing the AB-006a Antibiotic.

The two fractions thus collected were desalted by passing them separately through a column, having an inner diameter of 3.5 cm and 25 cm in length, filled with 80 g of resin XAD-4 and by eluting them with a 1:1 mixture of acetonitrile/water.

Then the eluates were concentrated to dryness thereby obtaining 60 mg of pure AB-006a Antibiotic and 6 mg of pure AB-006b Antibiotic, which appeared as white-hazel powders.

The physical-chemical characteristics of the products have been set forth above.

EXAMPLE 2

Fermentation of Streptomyces s.p. NCIB 12425

A 500 ml flask, containing 50 ml of culture medium A described above, was innoculated with a part of the colony of strain Streptomyces s.p. NCIB 12425, drawn aseptically from a plate or a slant of medium A treated with agar.

This culture was subjected to incubation on a rotary shaker at 200 rpm, over 72 hours at 20° C.

At the end of this period the culture broth was centrifuged in order to remove the mycelium, and sent to biological testing.

EXAMPLE 3

Fermentation of Streptomyces s.p. NCIB 12425

A lyophilized phial of the strain of Streptomyces s.p. NCIB 12425 was opened aseptically and hydrated again with distilled water and the suspension thus-obtained was used to innoculate a 20 ml test tube containing 5 ml of culture medium C, described above.

The culture was subjected to incubation on an oscillatory shaker at 50 o.p.m. at 20° C. over 72 hours.

The culture thus obtained was utilized to innoculate a 500 ml flask containing 100 ml of culture medium B, as described above. Afterwards it was subjected to incubation, under the same conditions of Example 2, for 96 hours.

What is claimed is:

1. AB-006 Antibiotics obtainable by aerobic controlled culture of Streptomyces s.p. NCIB 12425, or of an equivalent mutant thereof, in an aqueous nutrient culture medium containing sources of carbon, nitrogen and inorganic salts until a substantial antibiotic activity is obtained, and subsequent recovering said antibiotics having the following characteristics:

ultraviolet maximum absorbence of 1.50 at 272 nm;

infrared absorption maxima (cm$^{-1}$): 3700-3060; 2970; 2930; 2980 (shoulder); 1685; 1635; 1570-1505; 1455; 1435 (shoulder); 1385; 1355-1310; 1255 (shoulder); 1235; 1100; 1085-1000; 975; 875; 850; 820; 750.

2. AB-006a Antibiotic, a component of the AB-006 Antibiotics, which is a solid characterized by:

(a) a good solubility in dimethylsulfoxide and in mixtures ethanol/water (1:1, v/v) or methanol/water (1:1, v/v), poor solubility in water, ethanol or methanol;

(b) approximate elemental analysis in percentage: carbon 54.94, hydrogen 8.64, nitrogen 1.08;

(c) molecular weight of about 1203;

(d) ultraviolet maximum absorbance of 1.27 at 272 nm;

(e) infrared absorption maxima (cm$^{-1}$): 3700-3060; 2970; 2930; 2980 (shoulder); 1685; 1635; 1570-1505; 1455; 1435 (shoulder); 1385; 1355-1310; 1255 (shoulder); 1235; 1100; 1085-1000; 975; 875; 850; 820; 750;

(f) NMR spectrum of $^1$H, main peaks:

δTMS (ppm): 0.68 (d, 3H); 0.71 (d, 3H); 0.78 (d, 3H); 0.83 (d, 3H); 0.89 (d, 3H); 0.92 (d, 3H); 1.00 (d, 3H); 1.05 (d, 3H); 1.1-1.65 (14H); 1.69 (s, 3H); 1.93 (s, 3H); 2.00-2.55 (~6H); 2.81 (m, 2H); 3.25-3.54* (5H); 3.55-4.00 (~11H); 4.02-4.89 (22H among which 17 H are mobile); 4.19* (m, 3H); 4.42* (d, 1H); 4.69* (s, 1H); 5.11 (t, 1H); 5.32 (d, 1H); 5.44 (m, 4H); 5.53 (s, 2H); 6.26 (dd, 1H); 6.46 (dd, 1H); 7.11 (d, 1H); 7.67 (s, 2 mobile H);

(g) NMR spectrum of $^{13}$C, main peaks:
δTMS (ppm): 9.66; 9.77; 10.30; 10.55; 11.37; 11.61 12.53; 15.00; 16.81; 29.03; 29.16; 29.58; 32.28; 32.50; 39.20*; 39.38* 39.68*; 41.74*; 42.01* 42.26*; 42.46*; 42.63*; 45.95; 61.30; 63.84; 65.19; 66.69; 66.81; 67.11; 67.36; 70.14; 70.38; 70.58; 71.10; 71.59; 72.89; 73.63; 73.77; 74.54; 75.80; 81.02; 95.82; 120.90; 122.86; 124.23; 125.05; 129.56; 131.19; 132.43; 132.78; 138.00; 138.65; 144.02; 148.17; 167.22;

(h) Rf values by means of TLC on Merk-Shuckard 60F 254 plate;
0.34 in n-butanol: acetic acid: water, 3:1:1;
0.20 in n-butanol: acetic acid:water,ethanol, 38:10:50:2;

Rf values by means of reversed phase chromatography on Merk-Shukard RP-18F 254 plates;
0.20 in 1% (W/V) ammonium carbonate in water: tetrahydrofuran, 1:2;
0.09 in tetrahydrofuran: trifluoroacetic acid 0.14 mM in water: methanol, 3:6:1;
0.58 in monobasic pottassium phosphate 33 mM + tetramethylammonium chloride 10 mM in water: methanol 1:4;

(i) Rt of 10.75 minutes by means of reversed phase HPLC on column ROSIL C18, precolumn Guard Pak, RCSS C18, by eluting with a linear gradient from 40 to 70% of methanol in the mixture $KH_2PO_4$ 7 mM +$(CH_3)_4$ NCl 7 mM: methanol, 1:1, with a flow of 1:2 ml/minute; Rt of 7.1 minutes by means of reversed phase HPLC on a column Hibar Lil-Chro-Cart Li-Chrosorb RP18, precolumn Guard Pak RCSS C18, by eluting with 0.1% ammonium carbonate in water: tetrahydrofuran, 65.35, with a flow of 1 ml/min.

3. AB-006b Antibiotic, a component of the AB-006 Antibiotics obtained by aerobic controlled culture of Streptomyces s.p. NCIB 12425, or of an equivalent mutant thereof, in an aqueous nutrient culture medium containing sources of carbon, nitrogen and inorganic salts until a substantial antibiotic activity and subsequent separation from A-006 mixture by reversed phase chromatography, the antibiotic being a solid having the following characteristics:

(a) ultraviolet maximum absorbance of 0.77 at 272 nm;
(b) infrared absorption maxima (cm$^{-1}$): 3700-3060; 2970; 2930; 2980 (shoulder); 1685; 1635; 1570-1505; 1455; 1435 (shoulder) 1385; 1355-1310; 1255 (shoulder); 1235; 1100, 1085-1000; 975; 875; 850; 820; 750;
(c) NMR spectrum of $^1$H, main peaks:
δTMS (ppm): 0.69 (d, 3H); 0.71 (d, 3H); 0.78 (d, 3H); 0.83 (d, 3H); 0.89 (d, 3H); 0.92 (d, 3H); 1.00 (d, 3H); 1.04 (d, 3H); 1.21 (s); 1.69 (s, 3H); 1.96; (s, 3H); 1.1–2.4 (~35H); signals at ppm: 1.21; 1.69; 1.93; 2.8 (m, 2H) included; 2.9–5.0 group of signals overlapped on mobile H ions; 3.3–4.0*; (~20H); 4.16* (m, 3H); 4.43* (d, 1H); 4.69* (s, 1H); 5.11 (t, broad, 1H); 5.2–5.8 (~10H); 6.26 (dd, 1H); 6.43 (dd, 1H); 7.12 (t, 1H);

(d) Rf values by means of TLC on a Merk-Shuckard 60F 254 plate:
0.39 in n-butanol: acetic acid: water, 3:1:1,
0.16 in n-butanol: acetic acid: water: ethanol: 38:10:50:2;

Rf values by means of reversed phase chromatography on a Merk-Shuckard RP-18F 254 plate:
0.43 in 1% (W/V) ammonium carbonate in water; tetrahydrofuran, 1:2;
0.13 in tetrahydrofuran: trifluoroacetic acid 0.14 mM in water: methanol, 3:6:1;
0.67 in monobasic potassium phosphate 33 mM × tetramethylammonium chloride 10 mM in water: methanol, 1:4;

(e) Rt of 8.25 minutes, by means of reversed phase HPLC on a column ROSIL C18, precolumn Guard Pak RCSS C18, by eluting with a linear gradient from 40 to 70% of methanol in the mixture $KH_2PO_4$ 7 mM × $(CH_3)_4$NCl 7 mM; methanol, 1:1, with a flow of 1.2 ml/minute; Rt of 6.0 minutes, by means of reversed phase HPCL on a column Hibar Li-Chro-CART Li-Chrosorb RP18, precolumn Guard Pak RCSS C18, by eluting with 0.1% ammonium carbonate in water: tetrahydrofuran, 65.35, with a flow of 1 ml/minute.

4. A process for the preparation of the AB-006 Antibiotics comprising the culture of Streptomyces s.p. NCIB 12425, or of an equivalent mutant thereof, under conditions of controlled aerobic fermentation, in an aqueous nutrient medium comprising assimilable sources of carbon, nitrogen and inorganic salts, till a substantial antibiotic activity is obtained, the subsequent recovery of said antibiotics by known methods and, optionally, the separation of the main components called AB-006a Antibiotic and AB-006b Antiobiotic as defined in claim 2 or 3.

5. A process according to claim 4, wherein the fermentation is carried out at temperatures ranging from 25° and 30° C.

6. A process, according to claim 4, wherein the fermentation is carried out at a pH ranging from 5 to 9.

7. A process according to claim 4, wherein the AB-006 Antibiotics are isolated from the fermentation broth by filtration and subsequently by chromatographic techniques.

8. A process according to claim 4, wherein the AB-006a and AB-006b Antibiotics are isolated by reversed phase chromatography in a silica gel column by using in the elution a linear gradient from 50 to 70% of methanol in a mixture consisting of water containing 33 mM of $KH_2PO_4$ and 10 mM of $(CH_3)_4$ NCl.

9. The method of combatting fungus infestations comprising applying a fungicidally effective amount of a compound selected from the group consisting of AB-006 Antibiotics, AB-006a Antibiotic, and AB-006b Antibiotic as defined in claim 1, 2 or 3, as fungicide, to an environment infested with such fungus.

10. The method of combatting insect infestations comprising applying an insecticidally effective amount of a compound selected from the group consisting of AB-006 Antibiotics, AB-006a Antibiotic, and AB-006b Antibiotic as defined in claim 1, 2 or 3, as insecticide, to an environment infested with such insects.

11. Fungicidal compositions containing active ingredient a fungicidally effective amount of a compound selected from the group consisting of AB-006 Antibiotics, AB-006a Antibiotic, and AB-006b Antibiotic as defined in claims 1, 2, or 3, together with inert solid or liquid vehicles and other additives.

12. Insecticidal compositions comprising an insecticidally effect amount of a compound selected from the group consisting of AB-006 Antibiotics, AB-006a Antibiotic, and AB-006b Antibiotic as defined in claims 1, 2 or 3, as insecticide in admixture with an inert carrier.

* * * * *